(12) United States Patent
Lai et al.

(10) Patent No.: US 6,284,195 B1
(45) Date of Patent: Sep. 4, 2001

(54) DISPOSABLE REACTION MODULE

(75) Inventors: Lih-Huey Lai, Taipei; Ruei-Hung Jang, HsinChuang; Shih-Chou Chen, Hsinchu, all of (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 09/236,320

(22) Filed: Jan. 25, 1999

(51) Int. Cl.⁷ .................................................. G01N 21/00
(52) U.S. Cl. ............................ 422/58; 422/63; 422/102; 422/103
(58) Field of Search ........................ 422/58, 102, 103, 422/63, 50, 64, 99, 111; 435/286.5, 91.2, 284, 287.2, 91.1; 436/48; 216/94; 356/246; 222/63

(56) References Cited

U.S. PATENT DOCUMENTS

| | | |
|---|---|---|
| 4,043,678 * | 8/1977 | Farrell et al. . |
| 4,275,822 * | 6/1981 | Juffa et al. . |
| 4,605,536 * | 8/1986 | Kuhnert et al. . |
| 4,783,413 * | 11/1988 | Suter et al. . |
| 4,889,692 * | 12/1989 | Holtzman . |
| 5,075,082 * | 12/1991 | Fechtner . |
| 5,098,666 * | 3/1992 | Meinz . |
| 5,320,808 * | 6/1994 | Holen et al. . |
| 5,786,182 * | 7/1998 | Catanzariti et al. . |
| 5,849,208 * | 12/1998 | Hayes et al. . |
| 5,856,174 * | 1/1999 | Lipshutz et al. . |
| 5,863,502 * | 1/1999 | Southgate et al. . |
| 5,882,903 * | 3/1999 | Andrevski et al. . |
| 5,908,599 * | 6/1999 | Behringer et al. . |
| 5,922,591 * | 7/1999 | Anderson et al. . |
| 5,989,499 * | 11/1999 | Catanzariti et al. . |
| 6,043,097 * | 3/2000 | Dumitrescu et al. . |

* cited by examiner

Primary Examiner—Jill Warden
Assistant Examiner—Brian Sines
(74) Attorney, Agent, or Firm—Dougherty & Troxell

(57) ABSTRACT

This invention relates to a disposable reaction module, capable of permitting small amount of test agents to mix with a reaction agent, having at least one test agent room, a reaction chamber capable of making fluid communication with said test agent rooms, and at least a gate room, situated between the reaction chamber and the corresponding test agent room. A piston is provided for controlling the flow of test agent into the reaction chamber. Being portable, the module is suitable for field test applications, especially without direct human contact, the module offers safer operations over those using conventional tubes and glasses.

2 Claims, 6 Drawing Sheets

DISPOSABLE REACTION MODULE

BACKGROUND OF THE INVENTION

1. Field of the Invention

This invention relates to a disposable reaction module and particularly to a reaction module for small amount of fluid that includes a plural number of test agent rooms which are able to communicate fluidly with a reaction chamber for performing tests with a high degree of safety, convenience and mobility.

2. Description of the Prior Art

Traditionally when there is a need to do chemical or biochemical testing, particularly field testing, people have to carry a variety of test glasses, tubes, graduated cup, burette, etc. These facilities and equipments are fragile and should be handled with great care. Moreover the chemicals and agents being used are mostly hazardous to human beings and their disposal after the test could easily produce a pollution problem. All this makes field testing tedious and high risk work begging for improvement.

SUMMARY OF THE INVENTION

In view of the aforesaid disadvantages, it is therefore an object of this invention to provide a disposable reaction module that holds required test agents in the module and releases the test agents to mix with a reaction agent when needed, thus offering a safe, convenient and mobile chemical and biochemical testing tool.

It is another object of this invention to provide a disposable reaction module that is portable to facilitate field testing.

It is a further object of this invention to provide a disposable reaction module that dispenses with measuring test agent procedure so that testing time may be greatly shortened.

It is yet another object of this invention to provide a disposable reaction module that can hold required test agents in advance in the module for shorting the total test cycle.

It is still another object of this invention to provide a disposable reaction module that can hold required test agents in the module according to desirable test procedures.

It is a yet further object of this invention to provide a disposable reaction module that is compact and small in size to facilitate carrying for field testing.

It is a still further object of this invention to provide a disposable reaction module that may be made by an integral molding process so that it may be mass produced at low cost with fewer components to enhance its mobility and convenience.

It is one more object of this invention to provide a disposable reaction module that is able to free people from direct contact with test agents for enhancing safety.

In order to achieve the objects set forth above, the reaction module according to this invention includes a reaction chamber and at least one test agent room that may be fluidly communicating with the reaction chamber. The reaction chamber and the test agent room are separated by a gate room which has a piston disposed therein for controlling fluid flow between the reaction chamber and the test agent room. The reaction chamber and the test agent room have respectively a reaction agent inlet and a test agent inlet to allow reaction agent and test agent be poured therethrough into the reaction chamber and the test agent room.

The piston has a piston passage to enable test agent to flow from the test agent room to the reaction chamber.

In the reaction agent inlet there is provided a check valve which includes an elastic arm to allow reaction agent to flow into the reaction chamber in only one way.

The gate room has a reaction chamber passage and a test agent room passage which are able to communicate with the piston passage to allow test agent to flow into the reaction chamber.

This invention also provides a method for making a disposable reaction module. The method includes the following steps: a) sealing a cover on a top of a body, b) placing a check valve in a check valve opening of the cover for allowing reaction agent to flow only one way into a reaction chamber, c) disposing at least one piston in a gate room located in the body, d) pouring test agent through at least one test agent inlet in the cover into a plural number of test agent rooms, and e) sealing the test agent inlet with a sealing member for preventing the test agent from spilling out.

BRIEF DESCRIPTION OF THE DRAWINGS

The invention, as well as its many advantages, may be further understood by the following detailed description and drawings in which.

DETAILED DESCRIPTION OF THE PREFERRED EMBODIMENT

The disposable reaction module according to this invention includes a reaction chamber which has a check valve located in a reaction agent inlet to enable reaction agent be poured into the reaction chamber in only one way, at least one test agent room which has a test agent inlet to receive test agent, a gate room located between the reaction chamber and the test agent room for holding a piston therein to control the flow of test agent from the test agent room to the reaction chamber, and a cover for sealing the test agent inlet to prevent the test agent from spilling out.

This invention may contain one or more test agents, and enables the required test agent to mix with a reaction agent to perform desired testing without people contacting the agents directly so that people are better protected from the agents. This module may be integrally made by an injection molding process so that it may be mass produced at low cost. The module may be made small in size and portable so that it is convenient to carry around for field testing and is easy to dispose after testing is completed.

Figure 1:
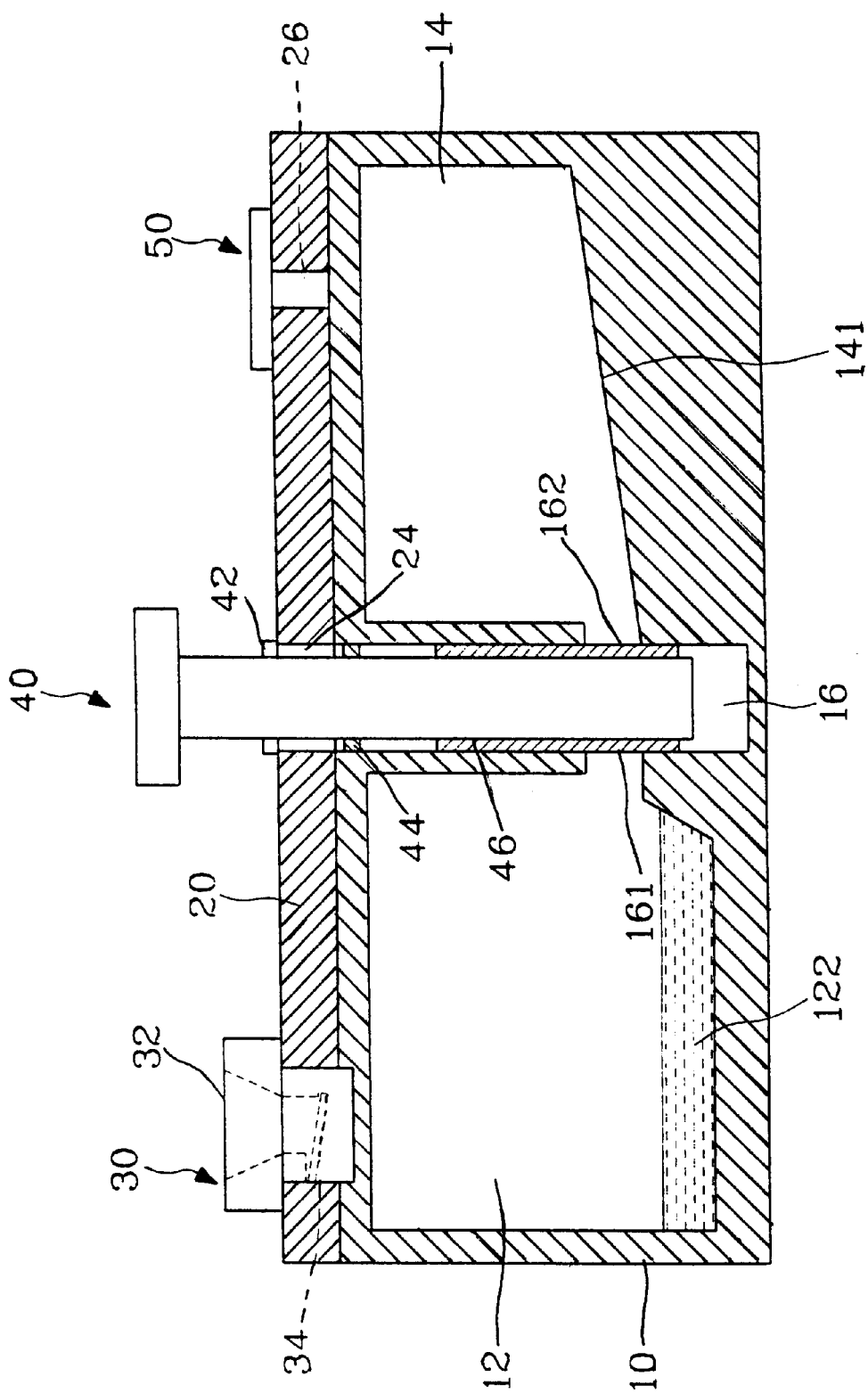
FIG. 1 is a sectional view of this invention.
Figure 2:
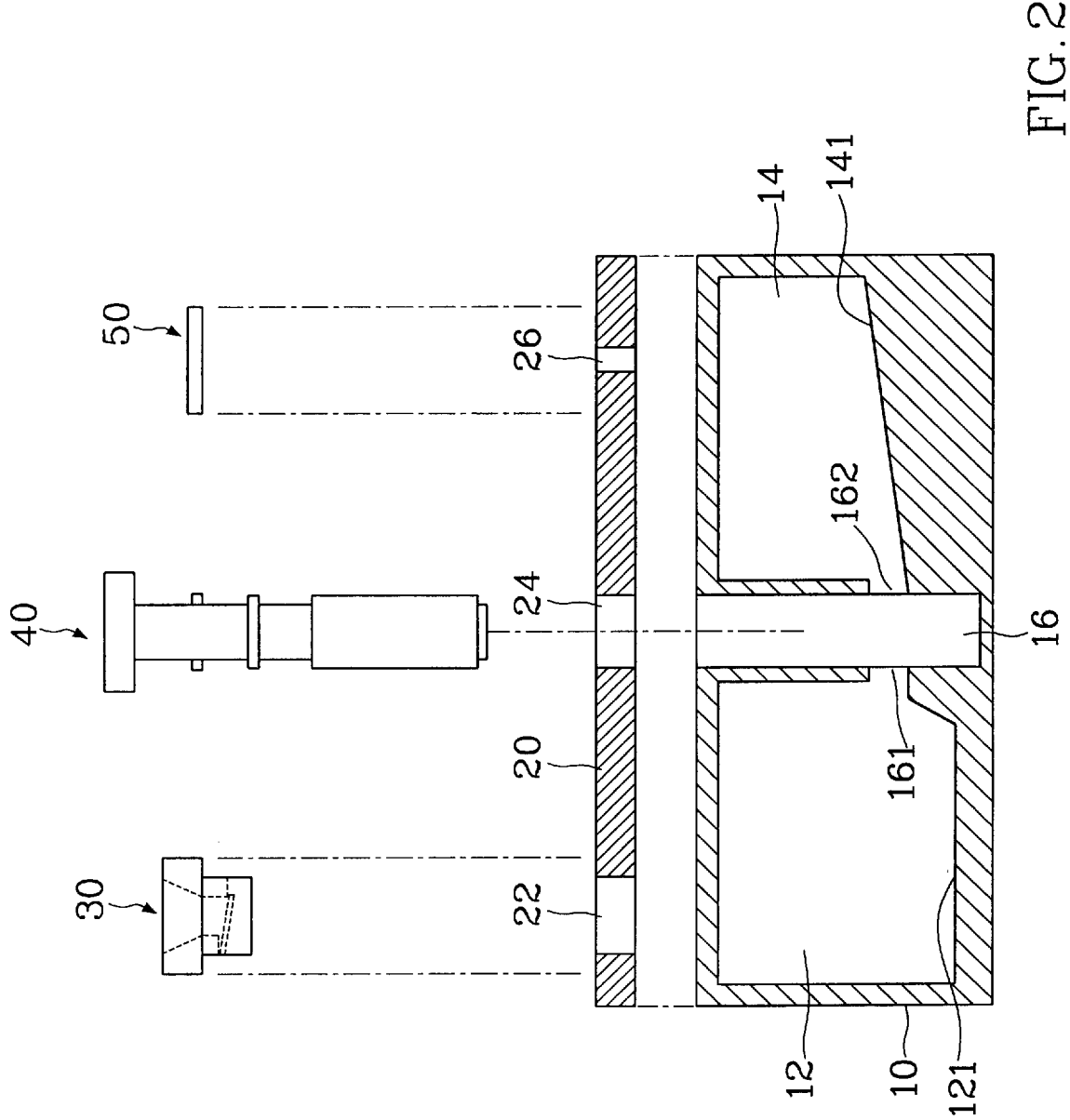
FIG. 2 is an exploded sectional view of this invention.

Referring to FIGS. 1 and 2, the reaction module according to this invention includes a body 10 having a reaction chamber 12 for holding a reaction agent, at least one test agent room 14 holding a testing agent and at least one gate room 16 located between the reaction chamber 12 and the test agent room 14. There is a cover 20 located at the top of the body 10. The cover 20 has a check valve opening 22 and at least one piston opening 24 and at least one test agent inlet 26. In the check valve opening 22, there is a check valve 30 which has a reaction agent inlet 32 to receive reaction agent 122 one way into the reaction chamber 12. Each gate room 16 has a piston 40 disposed therein for controlling flow of the test agent from the test agent room 14 to the reaction chamber 12. There is a sealing member 50 covering the test agent inlet 26 for preventing the test agent in the test agent room 14 from spilling out. The bottom 121 of the reaction chamber 12 is lower than that of the test agent room 14. The bottom 141 of the test agent room 14 is inclined toward the reaction chamber 12. Each gate room 16 has a reaction chamber passage 161 and a test agent room passage 162 formed respectively at both sides communicating with a through piston passage 48 (shown in FIGS. 6A and 6B) in the piston 40. Therefore when the piston 40 is turned to align the piston passage 48 with the passages 161 and 162, test agent held in the test agent room 14 may flow into the reaction chamber 12 and mix with the reaction agent 122 for performing the desired testing. However the reaction agent 122 which has a lower level than the bottom 141 of the test agent room 14 cannot flow into the test agent room 14.

Figure 3:
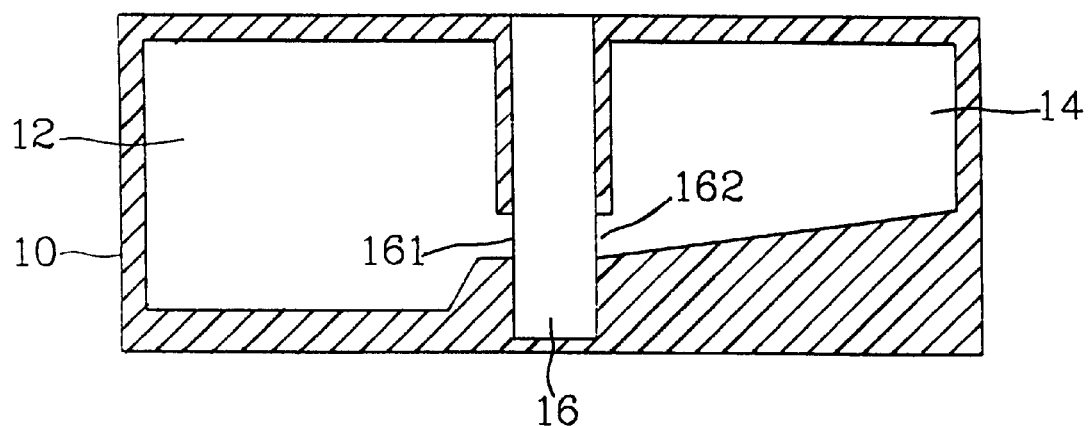
FIG. 3A is a sectional view of a body of this invention.
FIG. 3B is a top view of a body of this invention.
Figure 3:
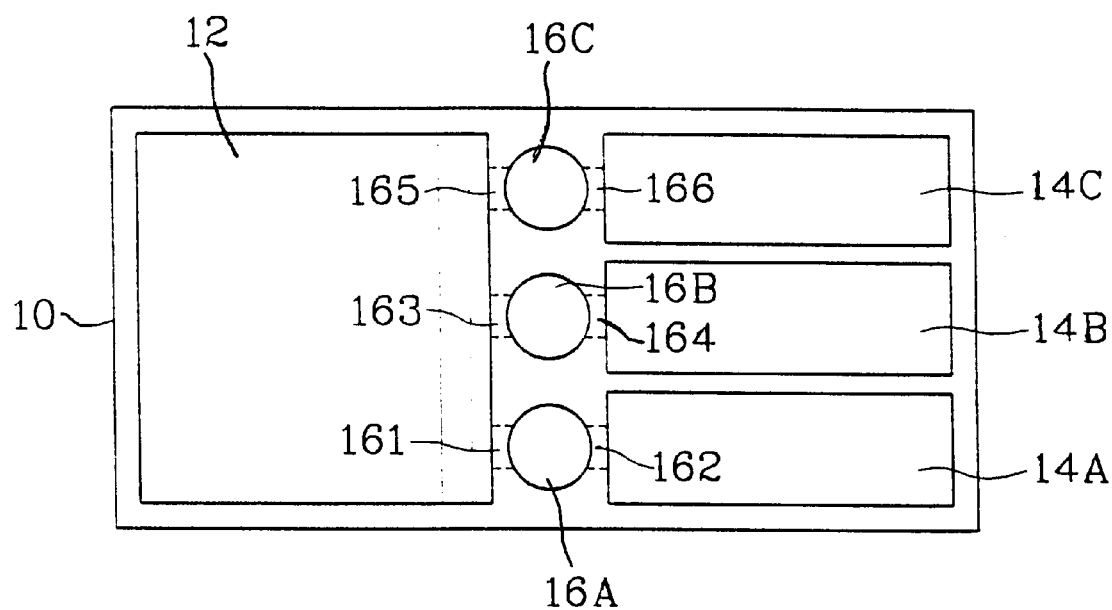

The following offers a more detailed description of the structure of this module. FIGS. 3A and 3B illustrate an embodiment of a body 14 which has one reaction chamber 12, three test agent rooms 14A, 14B, 14C, and three cylindrical gate rooms 16A, 16B and 16C. Each gate room is located between the reaction chamber and a test agent room and mates with the test agent room, and has a reaction chamber passage and a test agent room passage such as 161 and 162 for the gate room 16A, 163 and 164 for 16B, and 165 and 166 for 16C. The reaction chamber 12 has a lower bottom than that of the test agent room 14 which has the bottom inclined toward the reaction chamber 12 so that test agent may flow into the reaction chamber 12 from the test room, but not vice versa.

Figure 4:
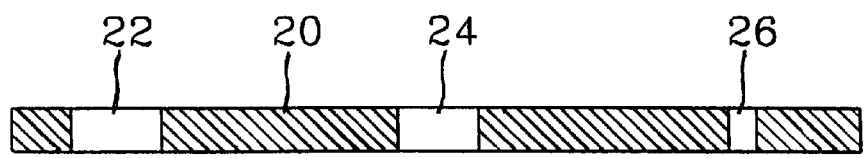
FIG. 4A is a sectional view of a cover.
FIG. 4B is a top view of a cover.
Figure 4:
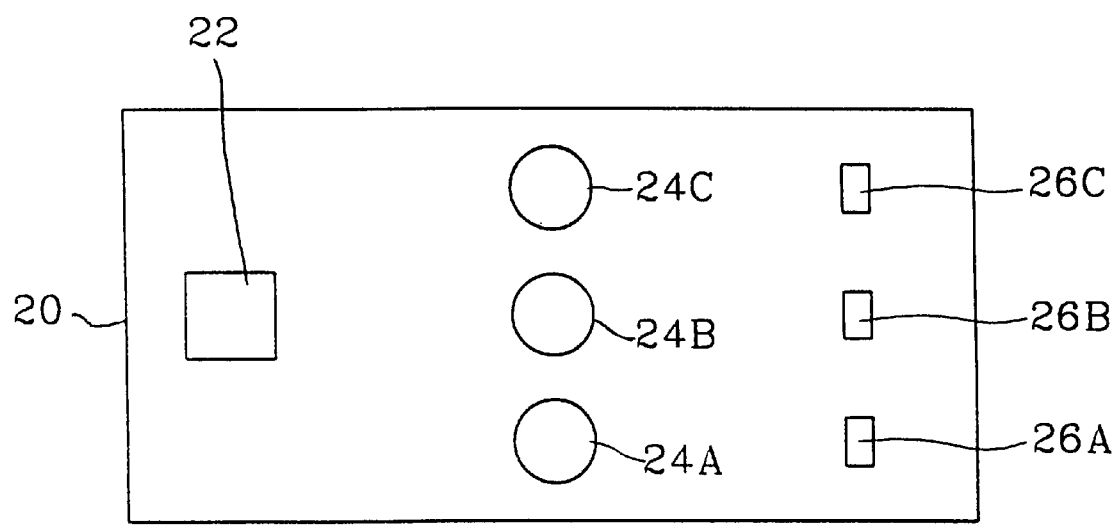

FIGS. 4A and 4B show an embodiment of a cover 20 which has a check valve opening 22, three round piston openings 24A, 24B, 24C and three test agent inlets 26A, 26B and 26C.

Figure 5:
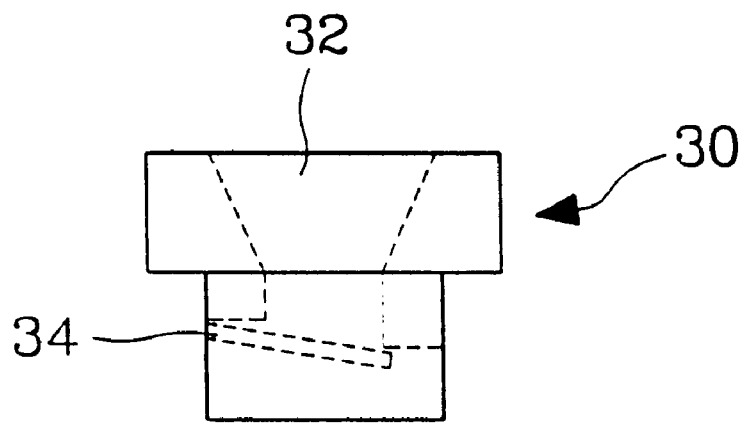
FIG. 5A is a side view of a check valve.
FIG. 5B is a top view of a check valve.
Figure 5:
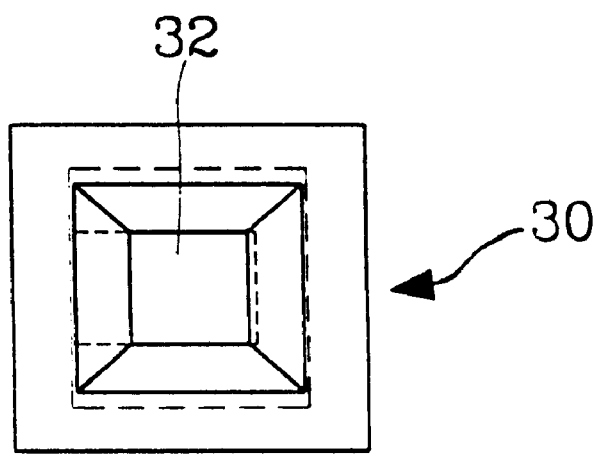

FIGS. 5A and 5B show a check valve 30 which has a funnel type reaction agent inlet 32 and an elastic arm 34 which may be opened under pouring pressure of the reaction agent but will be closed when the reaction agent stops pouring in. Once the reaction agent is held in the reaction chamber 12, it may be prevented from flowing out through the check valve 30.

Figure 6:
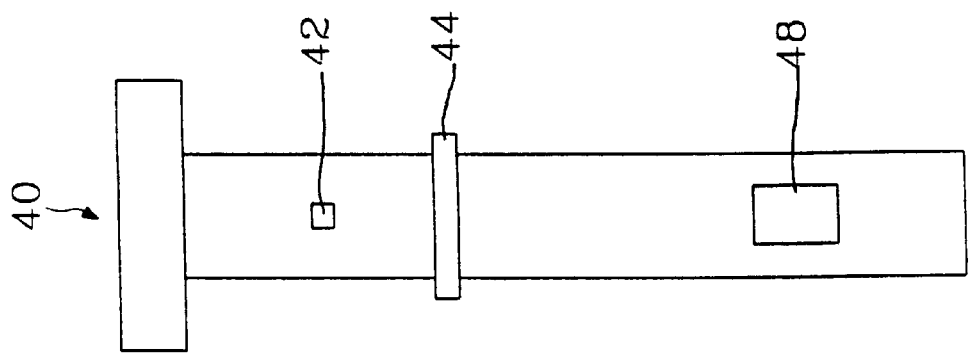
FIG. 6A is a side view of a piston.
FIG. 6B is a front view of a piston.
Figure 6:
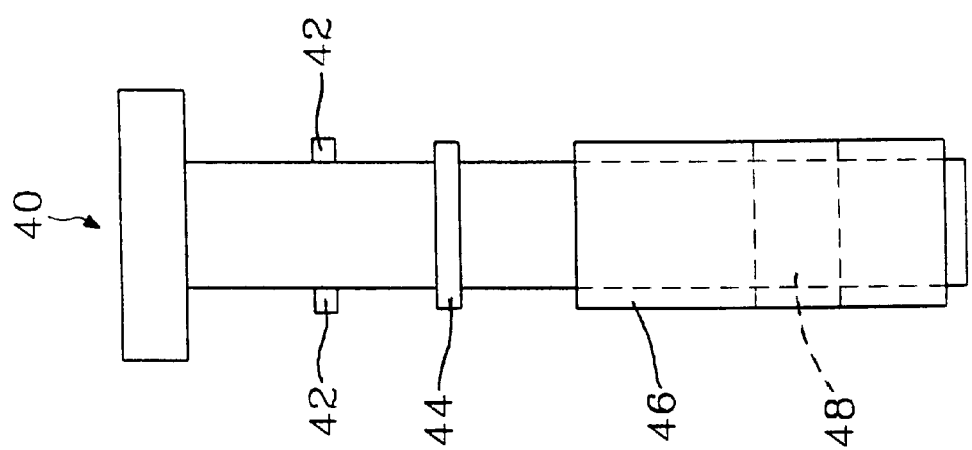

FIGS. 6A and 6B illustrates that the piston 40 is substantially a T-shaped cylindrical bar with a pair of holding stubs 42 to engage with the top surface of the cover 20 at the piston opening 24 to prevent the piston 40 from sinking into the gate room 16, an O-ring 44 to seal the gate room 16 for preventing test agent from leaking out, and a barrel 46 which engages tightly but is still able to rotate in the gate room 16. In the barrel 46, there is a through piston passage 48 which may align with the reaction agent passage 161 and the test agent passage 162 to form a faucet-like relationship to enable the test agent to flow or stop. The holding stubs 42, O-ring 44 and barrel 48 may be integrally formed with the piston 40. This invention also includes a manufacturing method for the reaction module as follow:

a) sealing the cover 20 over the top of the body 10;
b) installing the check valve 30 in the check valve opening 22 of the cover 20;
c) placing at least one piston 40 in at least one gate room 16 through at least one piston opening 24 in the cover 20;
d) pouring test agent into the test agent room 14 through the test agent inlet 26 until all test agent rooms containing required test agents.
e) placing the sealing member 50 over the test agent inlet 26.

Then the reaction module is ready to carry away for field test use. When in use, turn the piston 40 to align the piston passage 48 with the passages 161 and 162, test agent held in the test agent room may flow into the reaction chamber 12 to perform test desired. When the module contains more than one test agent rooms (such as 14A, 14B, and 14C shown in FIG. 3B), it may contain different test agents for a series of testing. The test may be done by turning the piston 40 without people being exposed to the reaction and test agents directly. It is therefore much safer than conventional testing using testing glass and tubes. The module may be integrally formed through an injection molding process. It may be produced at low cost in mass quantity. The module may be made compact and light weight, it is easier and safer to carry around for field test without the need to carry a lot of fragile and bulky testing tubes and glasses.

The body 10 may be made of light-permeating material and thus may be placed in a photometer or spectrograph for optical testing.

This invention may also perform biochemical tests for water, blood, urine and the like. A series of tests with different types of test agents may be held in this reaction module. The module is rugged to move and use, and safe to people who do the test. Disposal of this module is also much easier and convenient than conventional glass testing tools.

It may thus be seen that the objects of the present invention set forth herein, as well as those made apparent from the foregoing description, are efficiently attained. While the preferred embodiment of the invention has been set forth for purpose of disclosure, modifications of the disclosed embodiment of the invention as well as other embodiments thereof may occur to those skilled in the art. Accordingly, the appended claims are intended to cover all embodiments which do not depart from the spirit and scope of the invention.

What is claimed is:

1. A disposable reaction module, comprising:

a body having a reaction chamber for containing a reaction agent, the reaction chamber having a reaction chamber bottom, at least one test agent room for containing a test agent, the test agent room having a test agent room bottom inclined toward the reaction chamber and at least one gate room, said at least one gate room having a passage communicating with the reaction chamber and the at least one test agent room, the reaction chamber bottom being lower than the test agent bottom for enabling test agent to flow from said test agent room to said reaction chamber;

a cover, located on a top of said body, the cover having a check valve opening, at least one piston opening and at least one test agent inlet;

a check valve having a reaction agent inlet and an elastic arm, wherein said elastic arm is provided below said reaction agent inlet and comprises a passive one-way valve for allowing unidirectional flow of said reaction agent into said reaction chamber; and, a piston provided in each of the at least one gate room, the piston having a barrel on said piston and engaging said piston movably within said gate room, the piston and barrel having a through piston passage and movable between a closed position which closes the gate room passage, and an open position which opens the gate room passage to enable test agent to enter said reaction chamber, the piston further comprising a holding stub, provided on two opposite sides thereof, and formed integrally with said piston and located so as to rest on said cover, and an O-ring on said piston and engaging said piston and said body.

2. The disposable reaction module of claim 1, further comprising a plurality of sealing members located on said test agent inlet for preventing said test agent in said test agent room from spilling out.

* * * * *